United States Patent [19]
McWha et al.

[11] Patent Number: 5,480,389
[45] Date of Patent: Jan. 2, 1996

[54] METHOD AND APPARATUS FOR ADJUSTING THE LENGTH OF A COMBINED SPINAL-EPIDURAL NEEDLE

[75] Inventors: Keith McWha, Waldwick, N.J.; Nigel Talboys, Meylan, France; Joseph J. Gregg, Hasbrouck Heights; William T. Antoshkiw, Wayne, both of N.J.

[73] Assignee: Becton, Dickinson and Company, Franklin Lakes, N.J.

[21] Appl. No.: 287,995

[22] Filed: Aug. 9, 1994

[51] Int. Cl.⁶ .................................................. A61M 19/00
[52] U.S. Cl. ........................................... 604/165; 604/158
[58] Field of Search .................................. 604/158, 165, 604/274

[56]         References Cited

U.S. PATENT DOCUMENTS

| | | | |
|---|---|---|---|
| 2,922,420 | 1/1960 | Cheng | 604/158 |
| 3,356,089 | 12/1967 | Francis | 128/221 |
| 3,406,687 | 10/1968 | Moyer | 128/221 |
| 3,727,613 | 4/1973 | Sorenson et al. | 604/165 |
| 3,964,480 | 6/1976 | Froning | 128/215 |
| 4,230,123 | 10/1980 | Hawkins Jr. | 604/165 |
| 4,362,156 | 12/1982 | Feller Jr. et al. | 604/165 |
| 4,645,491 | 2/1987 | Evans | 604/158 |
| 4,760,847 | 8/1988 | Vaillancourt | 128/329 |
| 4,801,293 | 1/1989 | Jackson | 604/51 |
| 4,919,653 | 4/1990 | Martinez et al. | 604/117 |
| 4,940,458 | 7/1990 | Cohn | 604/51 |
| 5,085,631 | 2/1992 | Leighton | 604/28 |
| 5,106,376 | 4/1992 | Mononen et al. | 604/164 |
| 5,135,525 | 8/1992 | Biscoping et al. | 604/51 |
| 5,141,496 | 8/1992 | Dalto et al. | 604/117 |
| 5,195,526 | 3/1993 | Michelson | 128/654 |
| 5,246,425 | 9/1993 | Hunsberger et al. | 604/165 |
| 5,257,972 | 11/1993 | Gurmarnik | 604/51 |
| 5,312,375 | 5/1994 | Gurmarnik | 604/264 |
| 5,368,573 | 11/1994 | Andrew | 604/158 |
| 5,374,252 | 12/1994 | Banks et al. | 604/274 |
| 5,380,292 | 1/1995 | Wilson | 604/158 |

OTHER PUBLICATIONS

Use of 29-Gauge Spinal Needles and a Fixation Device With Combined Spinal Epidural Technique, J. Simsa, Acta Anaesthesiologica Scandinavica 38 (1994) pp. 439–441.

*Primary Examiner*—Paul J. Hirsch
*Attorney, Agent, or Firm*—Vincent A. Castiglione

[57]                ABSTRACT

A regulating device for adjusting the length of a combined spinal epidural needle and the method of practicing same is disclosed. In one variant, the regulating device features a pair of substantially concentrically disposed sliding members to which each of the epidural needle and spinal needle may be fitted. A locking actuation tab fitted to one of the sliding members is provided to control axial movement between the sliding members, thereby regulating the extension of the spinal needle relative to the epidural needle. The sliding members may be configured in a variety of shapes or dimensions to accommodate various combinations of spinal and epidural needles. The device may be provided pre-assembled with either one or both of the spinal needle or epidural needle, or it may be employed with a spinal needle, epidural needle, or both separately sourced.

25 Claims, 10 Drawing Sheets

METHOD AND APPARATUS FOR ADJUSTING THE LENGTH OF A COMBINED SPINAL-EPIDURAL NEEDLE

1. Field of the Invention

This invention relates to a combined spinal-epidural needle for delivery of a medicament to the subarachnoid space, and more particularly, to a method and apparatus for adjusting the extension of a spinal needle relative to the epidural needle during a procedure for delivering medicament to the subarachnoid space.

2. Background

As is known in the art, there exist two basic techniques for introducing injectable medicament into the spinal area of a patient. Both of these techniques have their own unique advantages and disadvantages and both can be used to create spinal anesthesia or analgesia. In both of these procedures, of course, the medicaments can be any type of liquid therapeutic material including antibiotics, steroids or the like. In general, however, the medicaments are agents used for anesthesia and/or analgesia.

The first procedure, known as the "epidural" technique, employs an epidural needle to deliver medicament to the epidural space of the patient. Certain epidural needles feature a curved distal end. Certain drawbacks exist with this technique. Because the medicament must percolate through semi-liquid fat to reach the nerve roots, the onset of the anesthetic block is oftentimes slow. Moreover, the potential exists for toxicity caused by the relatively large doses of medicament necessary to obtain an adequate block. After the initial dosage, a catheter is oftentimes inserted through the epidural needle into the epidural space to provide sustained or prolonged anesthesia/analgesia to the patient.

The second procedure, known in the art as the "spinal" or "subarachnoid" technique, typically employs a relatively small gauge needle to deliver medicaments directly to the subarachnoid space of the spinal column. Because the anesthetic is delivered directly to the nerve roots, the onset of anesthetic effect is quite rapid, and the block achieved by the spinal technique is often deeper than that possible employing the epidural technique.

The major disadvantage of the spinal technique relates to postoperative side effects. Unlike the epidural procedure, in the spinal technique, the dura mater must be punctured to reach the subarachnoid space. The resultant leakage of cerebrospinal fluid ("CSF") through the puncture oftentimes leads to severe postoperative headaches, known as "postdural puncture headache" ("PDPH"). In addition, while hypotension can result from either of the epidural or spinal techniques, it is believed that the rapid onset of the block in the spinal procedure causes a higher degree of hypotension than the epidural technique. Moreover, unlike the epidural procedure, which typically employs a catheter for continuous epidural blockage, a single shot spinal needle is often unable to extend the anesthetic block, once fixed.

A survey of previous patent literature reports in this general area may be found, for instance, in U.S. Pat. No. 5,085,631, which is directed to a method for placement of a subarachnoid catheter that utilizes a three component apparatus having an outer needle, an inner needle, and a catheter intermediate the two needles.

In order to alleviate the disadvantages associated with both procedures while providing the advantages of each, a combined spinal-epidural technique, or "CSE", has been developed. In CSE, an epidural needle is inserted into the patient in the usual manner and advanced to the epidural space without puncturing the dura mater. Next, steadying his or her hand against the patient's back and using the fixed epidural needle as an introducer, a smaller gauge spinal needle is inserted through the lumen of the epidural needle and advanced so that the distal end of the spinal needle crosses the epidural space. The practitioner, relying on his sense of touch, continues to insert the spinal needle until the distal end is felt to puncture the dura mater and enter into the subarachnoid space. A "pop" sensation is often felt at the hub of the spinal needle by the practitioner when the dura mater has been punctured. As confirmation of proper placement in the subarachnoid space, the practitioner will normally look for the appearance of CSF at the proximal end of the spinal needle by removing the stylet of the spinal needle.

Spinal anesthetic is administered in the usual manner, and the spinal needle is then withdrawn without displacing the epidural needle. Next, an epidural catheter is introduced through the epidural needle into the epidural space, and the epidural needle is thereafter removed from the back of the patient. Lastly, the epidural catheter is secured in place by taping same to the back of the patient.

In general, the CSE technique provides the practitioner with the benefits associated with the individualized epidural or spinal techniques while offsetting the disadvantages experienced by each. The surgeon is able to gain the advantages of rapid onset of a deep block provided by the spinal procedure. The epidural catheter serves to provide sustained anesthetic effect and extend the block provided by the spinal anesthetic. The catheter also enhances the practitioner's options and choices in administering operative anesthetic or postoperative pain relief. For example, the practitioner is able to administer a spinal anesthetic alone or in combination with epidural anesthetics and/or analgesics. Moreover, the practitioner can choose from a variety of medicaments or combinations thereof, with various rates of delivery, not being limited by the single injection of the spinal technique alone.

While providing the practitioner with a ready way to administer quality anesthetic relief to the patient, a number of drawbacks exist with current CSE practice. The CSE procedure is typically dependent on the individualized practitioner's experience with the method which, in ram, depends on the number and types of patients the doctor has had experience with. The exigencies of the operating environmental also greatly affect the procedure. As previously explained, CSE is performed by the relative insertion of two needles of differing gauges. Because the spinal needle is free to slide within the epidural needle, which itself is only retained by the dura mater once inserted, the danger exists that the spinal needle will be displaced during administration of the anesthetic. Thus, the doctor is required to utilize both hands, one to steady the spinal needle against the patient's body, the other hand to steady the syringe attached to the proximal end of the spinal needle. He must also utilize both hands when locking the spinal needle into place with the epidural needle. Because the doctor must steady his or her hand against the patient's back during insertion, smooth relative sliding is oftentimes difficult to achieve. Adequate tactile feedback, necessary to permit the practitioner to assess relative needle insertion, is also heavily dependent on the exigencies of the operating environment, which can vary at a moment's notice.

In addition, it will be observed that human body structures differ. The relative dimensions of the body, and particularly those defining the epidural space, the thickness of the dura mater, and the distance to the subarachnoid space, will vary. The doctor's appreciation of these dimensions is critical to proper placement of the needles in the appropriate locations, and in particular, to avoid inadvertent puncture of the dura mater.

Moreover, the practitioner must not only has to rely on his relative experience to make sure that the spinal needle is extended sufficiently through the dura mater, he must do so with two separate needles that may not often provide him with either sufficient tactile feedback or a discernible way to gauge relative insertion. A typical pencil-point spinal needle such as a Whiracre needle cannot always aspirate CSF, even when the dura mater is felt to "pop." In this situation, to be absolutely sure that the needles are properly placed, the practitioner must often withdraw both needles, repositioning them to reidentify the epidural space and, hence, the subarachnoid. This can cause unnecessary discomfort to both patient and practitioner.

Furthermore, in some situations practitioners will not need the full degree of spinal needle extension provided when the hubs of the spinal and epidural needles engage. When this type of situation occurs, the practitioner is forced to overcome a potentially unsafe and unsecure condition caused by a portion of the spinal needle protruding unsupported from the hub of the epidural needle.

The aforementioned difficulties can be amplified in that CSE is sometimes performed with individualized epidural and spinal needles sourced from different manufacturers. In these cases, owing to differing dimensions, tolerances, quality of finish or the like, precise sliding action between the needles may be compromised. Moreover, the hubs of differing spinal and epidural needles do not often fit, so that the practitioner cannot be sure of the relative extension achieved by the spinal needle. This can also affect the ability of the practitioners to rotate the spinal needle within the epidural needle in the locked state, useful if the practitioner suspects that the ports of the spinal needle are being blocked by the flap created in the dura mater during entry, or where the practitioner desires to better direct the extent of the anesthetic block provided by the spinal needle. The practitioner might wish to rotate the spinal needle so that the distal point is directed around the four quadrants of the subarachnoid space in an attempt to detect CSF. Faulty hub fit in the locked condition hampers the practitioner's ability to exploit the benefits of rotation.

Some manufacturers have begun to market matched sets of spinal/epidural needles to provide good hub fit and establish a predetermined amount of extension between the spinal and epidural needles when both hubs engage. While to a certain extent alleviating some of the problems encountered with "mixing" needles, the practitioner is still constrained by a fixed extension when the hubs interlock. For some patients, the fixed extension may still be inadequate to reach the dura mater, while for others it may be more than necessary.

Certain attempts in the art have sought to regulate the insertion or placement of a needle into the body. For instance, U.S. Pat. No. 4,940,458 is directed to a placement system for an epidural needle. An internally threaded barrel is provided to guide the externally threaded epidural needle via a knurled wheel at the proximal end of the epidural needle. A pressure monitor serves to advise the practitioner when the epidural needle has entered the epidural space. U.S. Pat. No. 5,312,375 is directed to a set for spinal anesthesia employing an introducer needle and a spinal needle. Either a screw or a toothed clamp arrangement may be provided to secure the spinal needle relative to the introducer needle once the spinal needle has been inserted through the dura mater. An analogous technique employing a metallic wing fixed to the epidural needle, with a relatively large L-shaped metallic bar engaged to the wing with two screws to fixedly adjust the position of the spinal needle relative to the epidural needle, has recently been proposed. See J. Simsa, "Use of 29 gauge spinal needles and a Fixation Device with Combined Spinal Epidural Technique", *ACTA Anaesthesiologica Scandinavia,* 1994 Vol. 38, pp. 439–441. The relative extension of the larger leg of the L-shaped bar past the wing is indicative of the spinal needle extension. Once the spinal needle has been extended to its desired position, a screw on the wing is tightened; two hands are required to operate this device. None of the aforementioned attempts sufficiently addresses the aforementioned problems of relative spinal needle insertion and inadequate (or nonexistent) tactile feedback currently experienced with the CSE procedure.

There exists a need, therefore, for a method and apparatus which will provide the practitioner with a ready way to support the spinal needle, gauge and insure precise insertion of the spinal needle through the epidural needle and into the subarachnoid space, maintain smooth sliding action and fit between the needles, and provide the practitioner with valuable tactile feedback during the procedure.

SUMMARY OF THE INVENTION

The present invention alleviates in great part the drawbacks associated with present CSE practice and provides the practitioner with a ready way to precisely monitor the insertion or removal of a spinal needle during CSE, all the while preserving good tactile feedback and fit between the spinal needle and epidural needle.

The invention is directed to a regulating device for extending and/or retracting the spinal needle relative to the epidural needle during CSE. The device, which may be provided as part of a CSE set, or with or attached to one of the spinal needle or epidural needles, or which can be provided as a separate unit for utilization with a separately sourced spinal needle or epidural needle or with a separately sourced CSE set, includes a pair of sliding members to which each of the epidural and spinal needles are separately fixed. The sliding members are disposed to permit relative sliding action between the spinal needle and the epidural needle. In one form, the sliding members may be configured as a pair of concentric tubes slidably disposed relative to one another. The interior surface of the outermost tube or, conversely, the exterior surface of the innermost tube, may be structured with a plurality of planar surface portions, with the opposing surface being relatively cylindrical. The mating of a planar surface portion with a rounded surface portion provides point contact between the inner and outer tubes, reducing the engagement surface area between the tubes, and, hence the frictional resistance between the tubes, providing for smoother sliding action and better tactile feedback to the practitioner.

An actuating tab may be provided for regulating operation of the device between a free position and a locking position. In one version, the tab may be biasingly fixed at one end to the outermost tube. The tab, operable with a one-handed effort by the practitioner, may include a mating portion for selectable engagement with the innermost tube responsive to the tab position selected by the practitioner. The mating portion may feature an engaging surface structured to permit secure locking action with a complimentary structured surface formed on or in the innermost tube. In one embodiment, the engaging surface may be formed as a male (or female) groove, with the tube surface formed with a series of female (or male) grooves located along the axis of the innermost tube. The series of grooves may be formed to correspond to a measured degree of extension of the innermost tube relative to the outermost tube which, in turn, relates to the degree of extension of the spinal needle relative to the epidural needle. Markings formed on the outside surface of the innermost tube provide the practitioner with visual indication of both the alignment of the distal tips of the spinal and epidural needles and with the relative extension length of the spinal needle relative to the epidural needle.

BRIEF DESCRIPTION OF THE DRAWINGS

The invention will now be described in greater detail by way of reference to the following drawings, wherein.

DETAILED DESCRIPTION OF THE INVENTION

Figure 1:
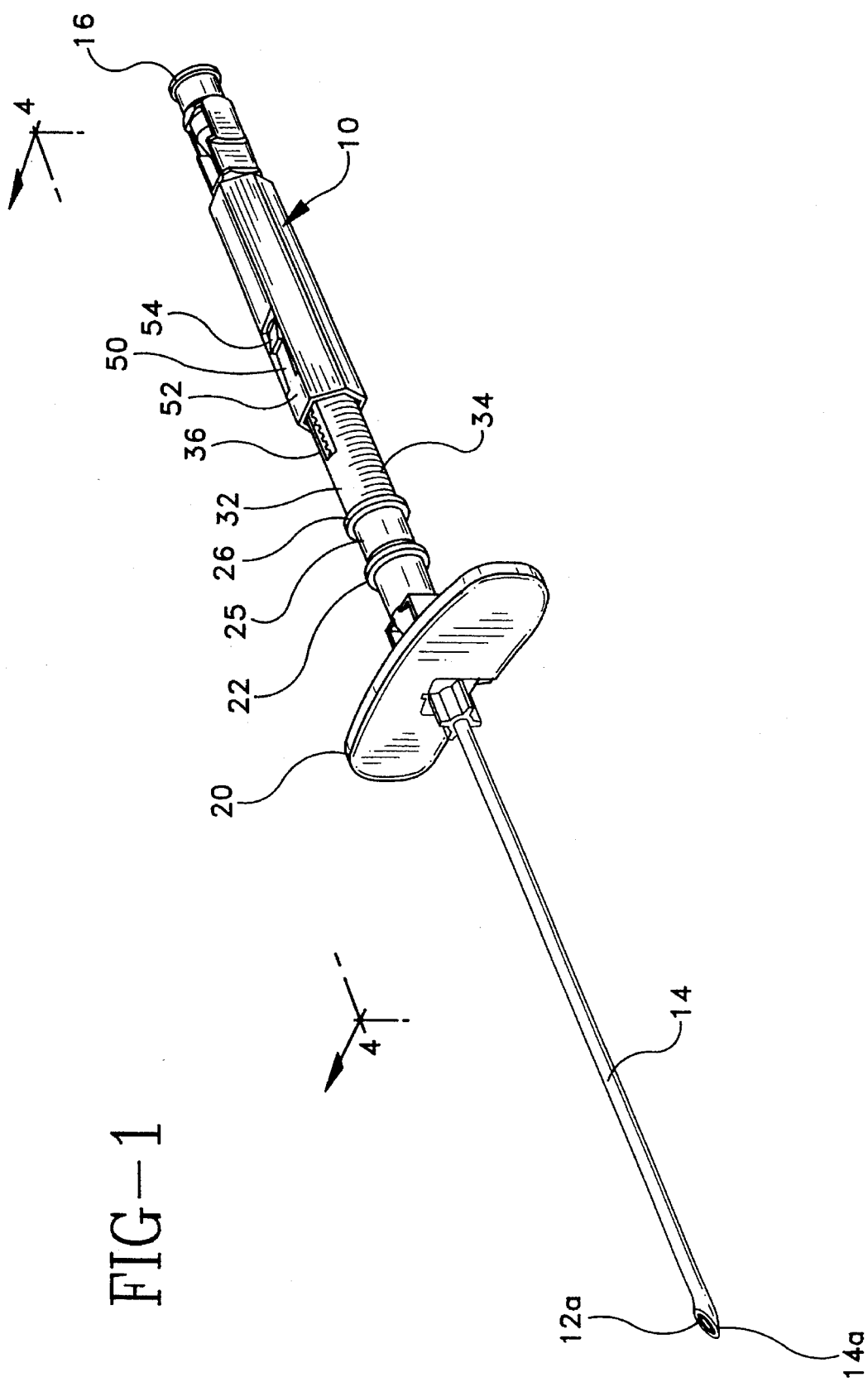
FIG. 1 is a perspective view of the regulating device of the present invention as utilized in conjunction with a CSE set, showing the spinal needle in a retracted state.
Figure 2:
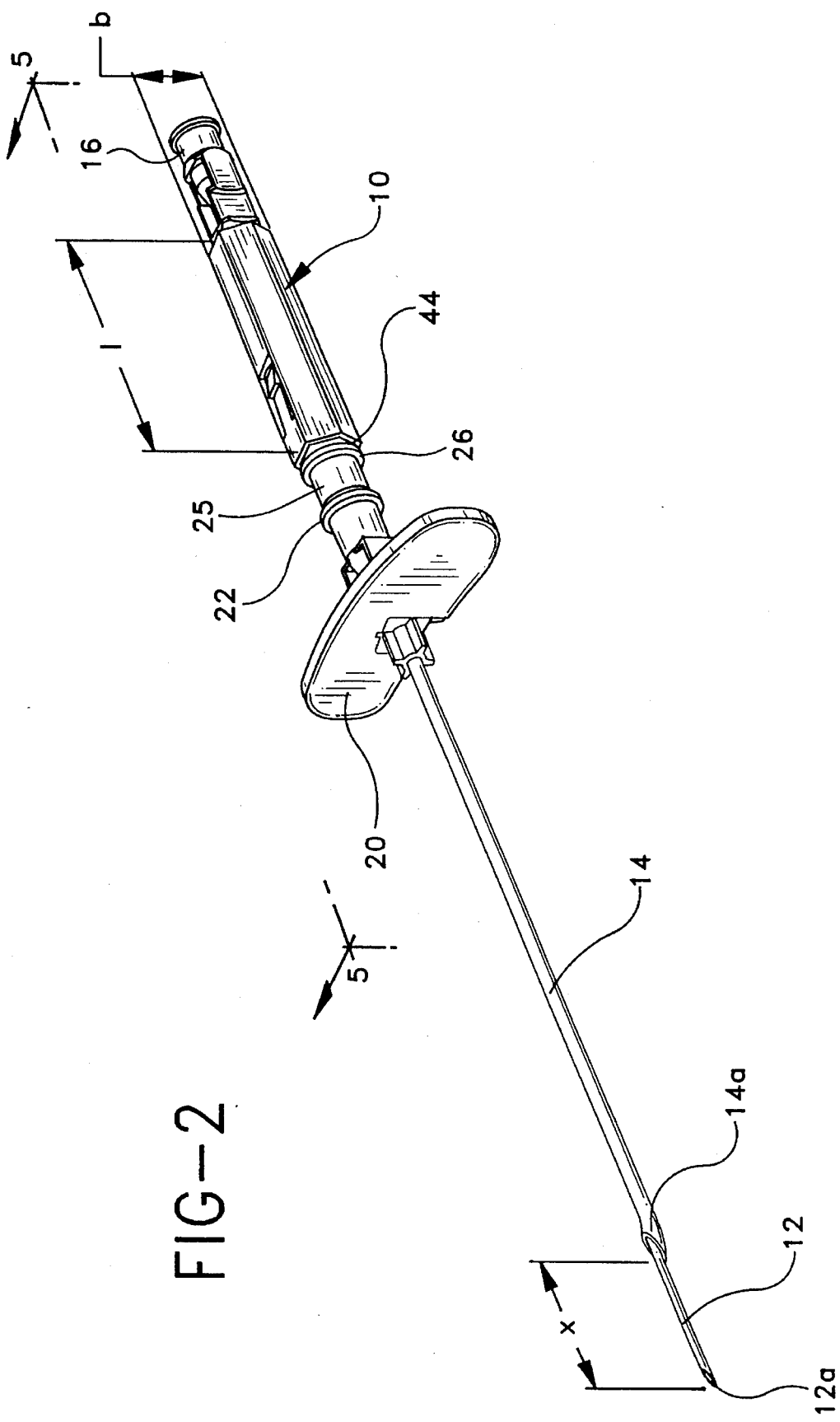
FIG. 2 shows a perspective view of the regulating device of the present invention, showing the spinal needle advanced through the lumen of the epidural needle.

Turning now to the drawings, wherein like numerals denote like components, FIGS. 1–9 depict one embodiment of a regulating device 10 for adjusting the extension length of a spinal needle 12 relative to an epidural needle 14 during a CSE procedure. It will be understood that while directed in particular to regulating the extension of a spinal needle relative to an epidural needle during a combined CSE procedure, the device is readily applicable to any device and/or procedure employing a needle through needle technique and employing regulation of needle length extensions during that technique.

Referring to FIGS. 1–5, the overall construction of the regulating device 10 in conjunction with an epidural needle 14 and the spinal needle 12 is illustrated. The epidural needle 14 will be well known to those skilled in the art and, in general, includes a distal end 14a and a lumen 15 extending through the length of the needle. As illustrated, the distal end 14a of the epidural needle may be curved for instance, to enhance a practitioner's efforts in directing placement of an epidural catheter (not shown) in the epidural space of a patient. A wing collar 20 may be provided to enable a practitioner to manipulate the needle and/or overall device during use. The epidural needle 14 further features a male luer connector 22 permitting attachment of the epidural needle 14 to an appropriate fitting, a syringe, or the like.

The spinal needle 12, equally well known to the skilled artisan, includes a distal end 12a together with a hub assembly 16. The hub assembly 16 features a stopper portion 18 configured to be placed within an appropriate fitting or the like. The spinal needle 12 may also be provided with a stylet (not shown), as is known to those skilled in the art, both for blocking the lumen 13 of the spinal needle during insertion and for providing the practitioner with a way to check for CSF during the procedure.

In general, the device 10 may be employed with any combination of spinal needle 12 and epidural needle 14. It has been found, however, that to accommodate most patients, useful ranges of the epidural needle 14 include lengths between 8 centimeters ("cm") (3.1496") to about 8.890 cm (3½"), while the spinal needle 12 can range from about 14.645 cm (5⁴⁹⁄₆₄") to about 15.558 cm (6⅛"). The spinal needle 12 can be provided in various standardized diametral sizes ("gauges") depending on the particular anesthetic application desired by the practitioner, but in general it has been found that spinal needles 12 between 22 gauge and 29 gauge will accommodate most applications. The following table provides diametral dimensions across the gauge range:

| Table of Hypodermic Tubing Nominal Sizes | | |
| --- | --- | --- |
| Gauge | Outside Diameter (mm) | Inside Diameter (mm) |
| 30 | 0.30 | 0.18 |
| 29 | 0.33 | 0.20 |
| 28 | 0.36 | 0.20 |
| 27 | 0.40 | 0.25 |
| 26 | 0.46 | 0.30 |
| 25 | 0.51 | 0.30 |
| 24 | 0.56 | 0.36 |
| 23 | 0.64 | 0.38 |
| 22 | 0.71 | 0.46 |
| 21 | 0.82 | 0.56 |
| 20 | 0.90 | 0.65 |
| 19 | 1.08 | 0.80 |
| 18 | 1.27 | 0.96 |
| 17 | 1.50 | 1.17 |
| 16 | 1.65 | 1.32 |

A general overall view of the regulating device 10 in conjunction with the spinal needle 12 and epidural needle 14 is broadly depicted in FIGS. 1–5. In the form depicted, the regulating device 10 includes a first sliding member such as an outer cylinder or tube 51 disposed in sliding relation to a second sliding member such as an inner cylinder or tube 32, each of which are respectively fixed to one of the spinal needle 12 or the epidural needle 14. While other configurations may be envisioned, as here depicted, the epidural needle 14 is mounted to the inner tube 32 via a hub fitting 25 disposed at the distal end of the inner tube 32. The hub fitting 25 includes a proximal end 26 configured to mate with a male luer extension 30 disposed at the distal end 28 of the inner tube, with the hub fitting 25 itself including a male luer fitting 24 at its distal end for snug insertion into the hub 22 of the epidural needle. It will be realized by those skilled in the art that the hub fitting 25 may be provided either as part of the regulating device 10 or as part of the epidural needle 14.

As herein illustrated, the spinal needle 12 may be secured to the outer tube 51 via its hub fitting 18 which may be configured for snug and secure engagement with the proximal end 46 of the outer tube 51. When assembled, the spinal needle 12 will project through the lumen 15 of the epidural needle 14, with the distal end 12a of the spinal needle axially extendible relative to the distal end 14a of the epidural needle by sliding action between the outer tube 51 and inner tube 32 of the regulating device. While various extension lengths "x" (see FIG. 2) of the spinal needle 12 relative to the epidural needle are possible depending on user need or desire, an extension length of approximately 1.501 cm (0.591") (inches) has been found to suffice for applications to most patients. However, one skilled in the art of catheters, needles and hypodermic delivery devices will recognize that for specialty applications such as neonales, pediatric patients, especially thin or obese individuals, and other specialty applications, it may be desirable to reduce or increase the sizes, gauges, component lengths, or extension lengths and/or other dimensions associated with the various components herein described for the specific application.

Turning our attention to construction of the regulating device, the inner tube 32 may be formed as a hollow cylindrical tube extending between a distal end 28 and a proximal end 29. The tube 37 can be formed from any appropriate rigid material including a medical grade plastic such as polycarbonate, a metal, or the like, and, if desired, can be formed through an injection molding process. The tube 32 features an axially extending slot 36 providing access to a structured interior surface 38. As better seen in FIGS. 4–7, the structured interior surface 38 may be formed as a plurality of concentric groove elements 38a formed along the axial length of the inner tube 32. The groove elements 38a may be formed in a variety of manners, such as male or female grooves; ramps or other similar projections; raised or recessed indentations; or various other configurations as may be envisioned by the skilled artisan. The spacing between the groove elements 38a may be either equidistant or non-uniform as need or desire dictate. While the structured surface 38 can be formed along the entire axial length of inner tube 32, it will be understood that the structuring may be effected along the axial length required to obtain the desired extension "x" of the spinal needle 12 relative to the epidural needle 14. While the overall length and diameter of the inside tube may be chosen as need or desire dictate, an outside diameter "a" (FIG. 1) of about 0.620 cm (0.244") and an overall length "c" (FIG. 3) of about 2.009 cm (0.791") measured between the distal end 28 and proximal end 29 should suffice for most applications. It will also be appreciated that when distal ends 14a, 12a of the epidural and spinal needles are aligned prior to use, a proximal length "d" (FIG. 3) should remain within the outside tube 51 to provide stability. Here, a length "d" of about 0.508 cm (0.200") may be provided for stability, with the remaining 1.501 cm (0.591") of the inner tube 32 length representing the relative extension of the spinal needle 12 relative to the epidural needle 14 in use.

A plurality of markings 34 may also be provided on the outside surface of inner tube 32 to help the practitioner gauge the relative extension of the outer tube 51 respective to the inner tube 32. The markings 34 may be calibrated, as need or desire dictate, to any standard of measurement, such as millimeters, centimeters or the like. As will be discussed in greater detail below, the markings 34 may be calibrated to the extension provided by the structured surface 38 of the inner tube and, in particular, individual markings 34a may be configured to correspond to individualized grooves 38a in the structured surface 38 to assist the practitioner in gauging the relative extension length "x" of the spinal needle 12 relative to the epidural needle 14.

The outer tube 51 includes a proximal end 46 and a distal end 44 and, as previously described, is disposed in sliding relation to the inner tube 32. Like the inner tube 32, the outer tube can be formed from a suitable material such as medical grade plastic, metal, or the like, and it can be injection molded. The outside surface 53 of the tube can be shaped in a variety of manners to enable secure gripping by the practitioner. Here, the outside surface is shaped as a hexagon, but other configurations are equally possible texturing. Moreover, the outside surface 53 can be textured or roughened to enhance one's grip on the device. The outer diameter "b" and the length "l" (FIG. 2) of the outside tube 51 can be constructed to any appropriate dimension both to provide easy one-handed manipulation by the practitioner and to accommodate the variously sized epidural needles 14/spinal needles 12 utilized as previously described. In general, an outside diameter "b" of about 0.856 cm (0.3371") and a length "l" of about 2.606 cm (1.026") will suffice for most practitioners.

As illustrated in FIGS. 1–5, the outer tube 51 features an interior surface formed as a plurality of planar surfaces 58 circumferentially disposed around the central axis of the outer tube 51. While here illustrated as formed with a hexagonal configuration having six planar surfaces 58, it will be understood and appreciated by those skilled in the art that the invention is not so limited, and that the interior surface may be configured with any number of planar surfaces such as pentagonal, octagonal, etc. as need or desire dictate.

Figure 7:
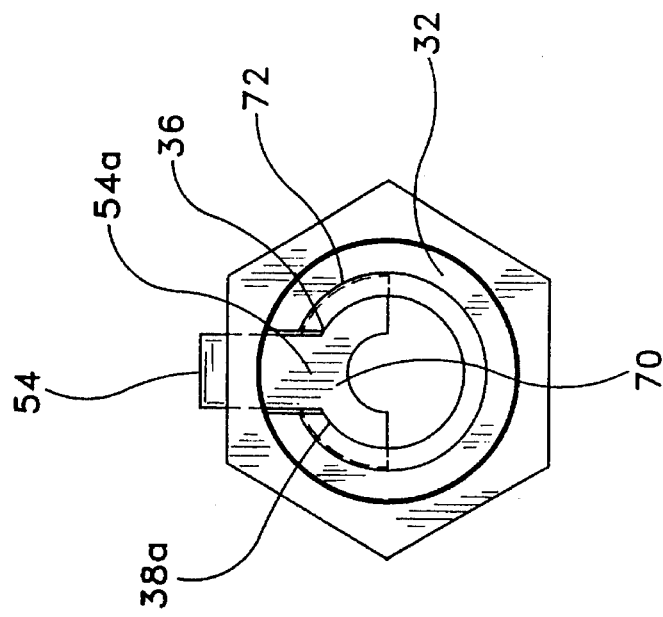
FIG. 7 is a rear view of the regulating device, as seen along line 7—7 of FIG. 3, showing engagement of the actuating tab with the innermost robe.
Figure 6:
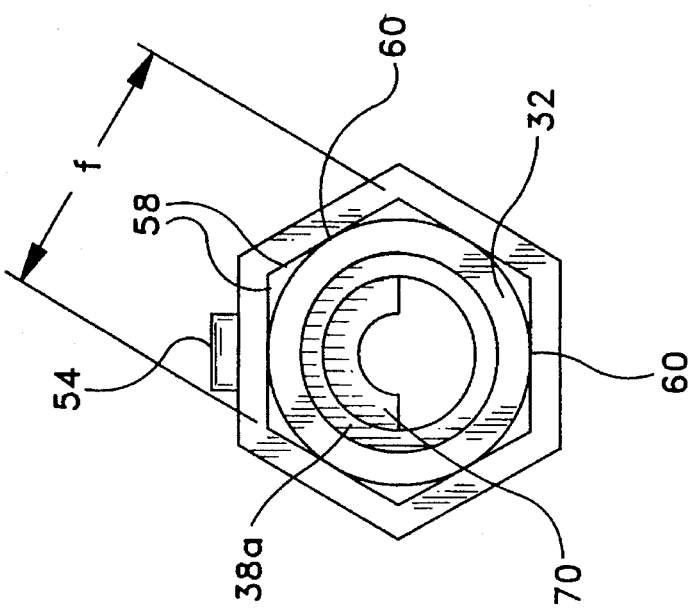
FIG. 6 depicts a frontal view of the regulating device, as seen along line 6—6 of FIG. 3, showing the point contact relationship between the innermost and outermost tubes.
Figure 9:
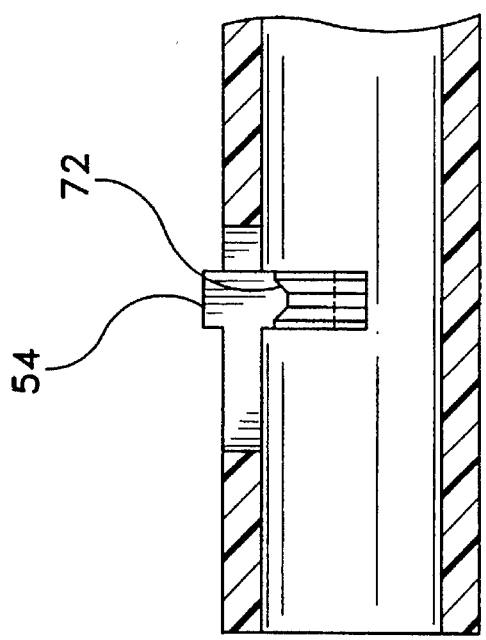
FIG. 9 is a partial cutaway side view of the regulating device showing the actuating tab and mating portion.
Figure 8:
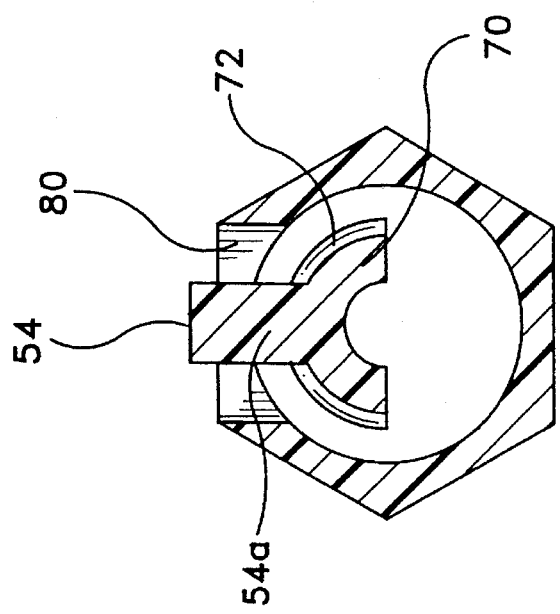
FIG. 8 is a cutaway view of the regulating device, as seen along line 8—8 of FIG. 4, with the innermost tube removed for clarity, showing the actuating tab and its mating portion as engaged with the innermost robe.
Figure 10:
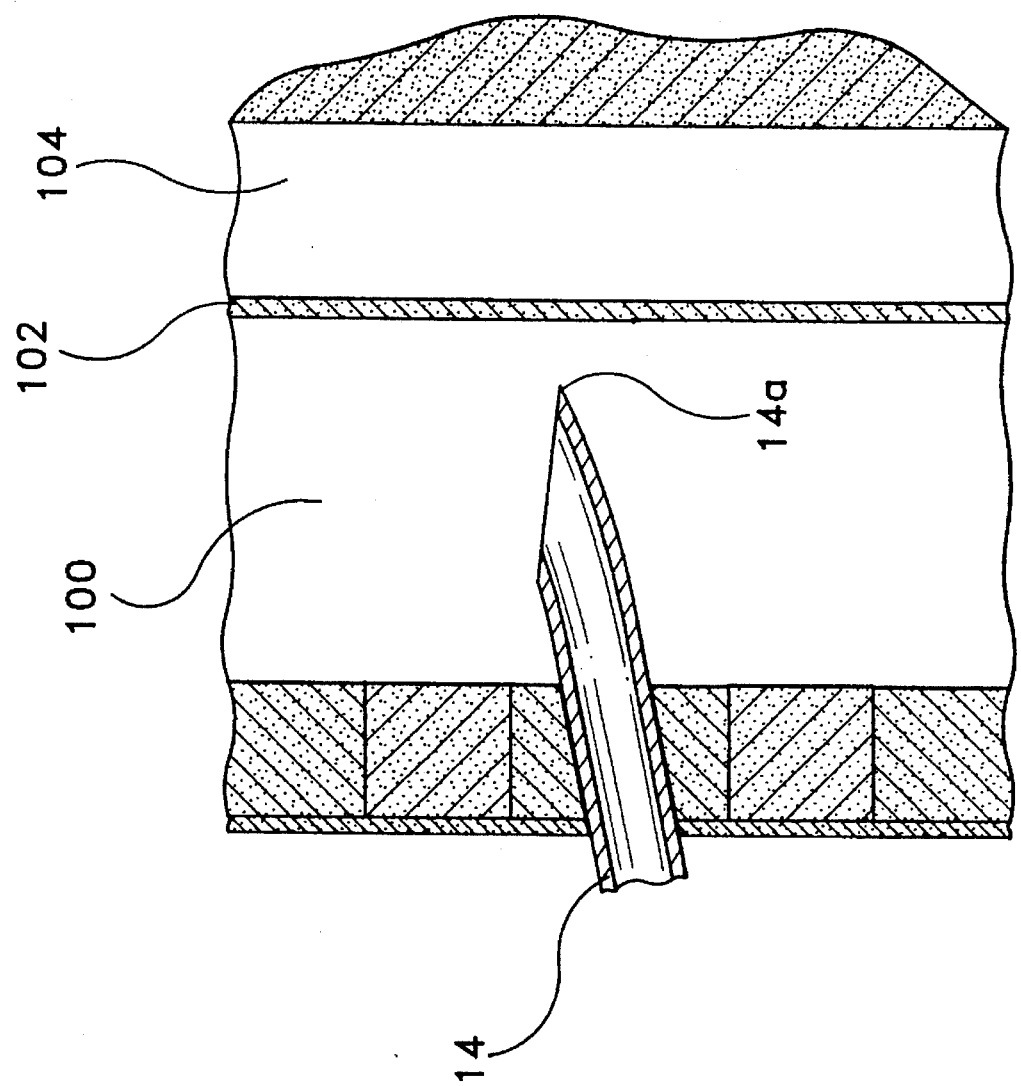
FIG. 10 is a side view illustrating placement of an epidural needle into the epidural space of a patient.

Referring to FIGS. 6–8, it will also be seen that the inner tube 32 is disposed within the outer tube 51 such that the outside surface 33 of the inner tube 32 is in substantial sliding contact with the planar surfaces 58 of the outer tube 51. A plurality of contact points 60 are established by the intersection of the relatively rounded outside surface 33 of the inner tube 32 and each of the planar surfaces 58. It will be appreciated that by this arrangement, the outside circumferential surface area of the inner tube 32 is disposed in sliding contact with the interior of the outer tube 51. By reducing the contact area between the tubes and, in particular, by providing sliding point contact between the inner tube 32 and outer tube 51, frictional resistance between the tubes is substantially reduced, thereby enhancing smooth sliding action between the tubes, and resulting in better tactile feedback to the practitioner.

While it is desirable to maintain a relatively close diametral tolerance between the inner tube 32 and outer tube 51 to promote stability and precise sliding action, the inside diameter "F" (FIG. 6) of the outer tube 51 should provide a slight clearance to prevent undue friction when sliding relative to the inner tube 32 Here, the diameter "F" may be configured to about 0.627 cm (0.247") to prevent frictional resistance with the inner tube 32 having, for instance, an outside diameter "a" of 0.620 cm (0.244").

It will be understood and appreciated that instead of providing the planar surfaces on the interior of the outer tube, with a rounded exterior surface on the inner tube, the plurality of planar surfaces may be structured on the exterior surface of the inner tube, with the interior of the outer tube rounded so as to provide point contact. As will be better evident from the discussion below, it will be further understood that the entire length of the outer tube 52 need not be structured with the planar surfaces 58. Rather, only the axial portion of the outer tube 51 which will be subjected to relative sliding motion respective to the inner tube 32 need be structured so as to provide the benefits described above. Thus, for extension "x" of 1.501 cm (0.591"), only an axial length of 1.501 cm (0.591") measured from the distal end 44 of the outside tube 51 need be provided with the planar surfaces 58.

Turning to FIGS. 1–9, and in particular to FIGS. 4–9, an actuating tab 50 is provided to enable the practitioner to regulate the axial position of the outer tube 51 relative to the inner tube 32 and, hence, to vary the extension of the spinal needle 12 relative to the epidural needle 14. For purposes of illustration, but not of limitation, the tab 50 is here illustrated configured as a cantilevered arm. However, it will be understood and realized by those skilled in the art that the tab 50 can be devised in numerous alternate manners. For instance, the tab 50 can be formed as a push-button configuration having, for instance, a spring or other biasing element for coordinating operation and use of the device, or the tab 50 can be formed as a sliding button or sliding tab configuration. Various other constructions as will be within the realm of the skilled artisan can be realized.

The actuation tab 50, which may be molded or otherwise formed as a portion of the outer tube 51, may be resiliently fixed at one end 52 to the outer tube. A finger tab 54 is provided at the second end of the tab 50, permitting one-handed operation by a practitioner to bias the tab between a locked position, wherein the outer tube 51 is fixed in axial relation to the inner tube 32, and an unlocked position, wherein the outer tube 51 is axially slidable relative to the inner tube 32.

The actuating tab 50 includes a neck portion 54a disposed both through a slot 56 formed in the surface 53 of the outer tube 51 and through the axial slot 36 formed in the inner tube 32. A mating portion 70 is provided at the end of the neck 54a in a manner so as to be located within the structured interior 38 of the outer tube 32. As here illustrated, the mating portion 70 may be configured as a relatively flat, semi-circular tab, to accommodate the relatively circular interior surface of the inner tube 32. However, other shapes or configurations of the mating portion 70 may be devised as need or desire dictate.

As shown, mating portion 70 includes a mating surface 72 for locking engagement with the groove elements 38a forming the structured surface 38. Here, the mating surface 72 is illustrated as a female groove formed in opposed mating relationship to the structured surface 38 of the outer tube 32. In particular, the groove 72 is dimensioned so as to lockingly mate with one of the individual concentric grooves 38a which, taken together, form the structured surface 38.

While the structured surface 38 is here illustrated as being formed along a major portion of the inner robe 32, as previously described it will be appreciated by those skilled in the art that the structured surface 38 can be formed in a variety of manners and/or configurations, as necessary or desired, so that the structuring need not encompass the entire inner circumferential area of the inner robe 32. For instance, the structured surface 38 may be provided on a portion of the surface area, such as on one quadrant of the circumferential surface area disposed within the interior of the inner tube 32. Thus, the mating portion 70 may be appropriately designed in order to mate with the portion of the inner circumferential area of the inner tube 32 which has been structured as previously described. It will further be appreciated that the mating surface 72 may be appropriately configured to the particular treatment and extent thereof chosen for the structured surface 38. For instance, if structured surface 38 were formed as a plurality of female groove elements 38a, the mating portion 72 may be configured as a male groove which is matingly disposed with the concentric female grooves 38a forming the structured surface 38. As the structured surface 38 may be devised in varying manners, the mating surface 72 may also be appropriately configured so as to matingly engage with the particular configuration chosen for the structured surface 38. Other variations and configurations may be envisioned by those skilled in the art.

Figure 3:
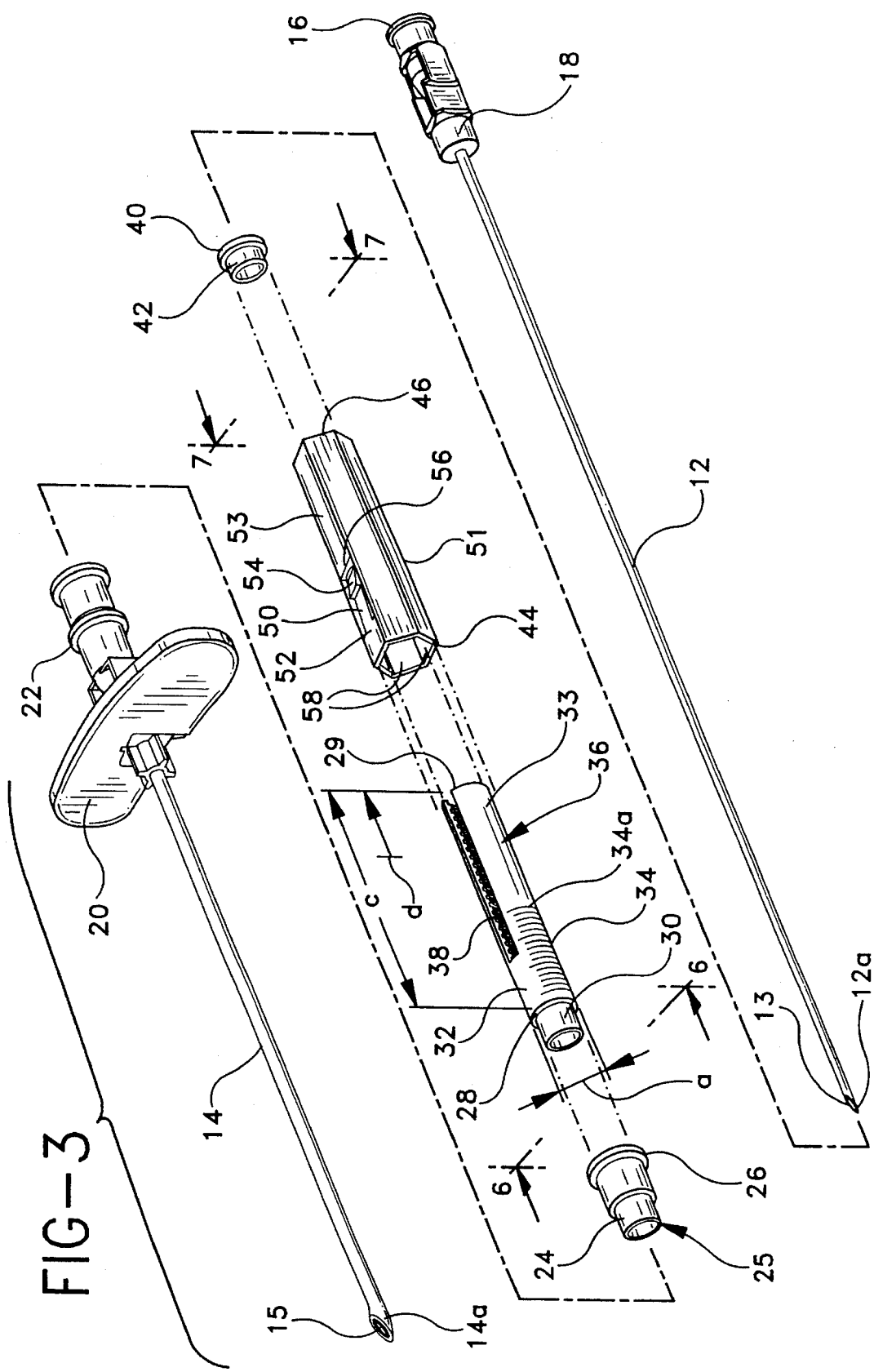
FIG. 3 depicts an exploded assembly view in perspective of the regulating device of the present invention.
Figure 4:
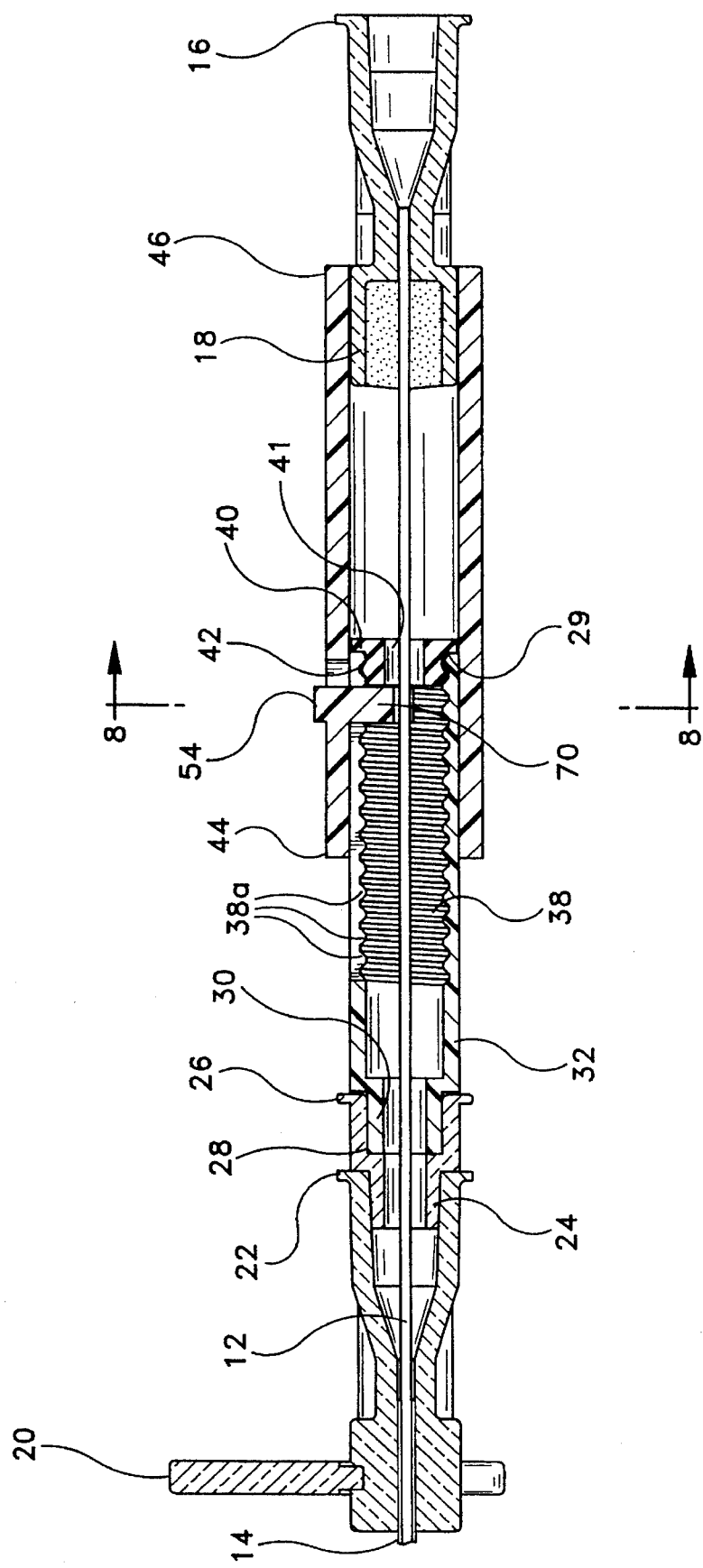
FIG. 4 illustrates a side view of the regulating device, as taken along line 4—4 of FIG. 1, showing the outermost tube in an extended state relative to the innermost robe.
Figure 5:
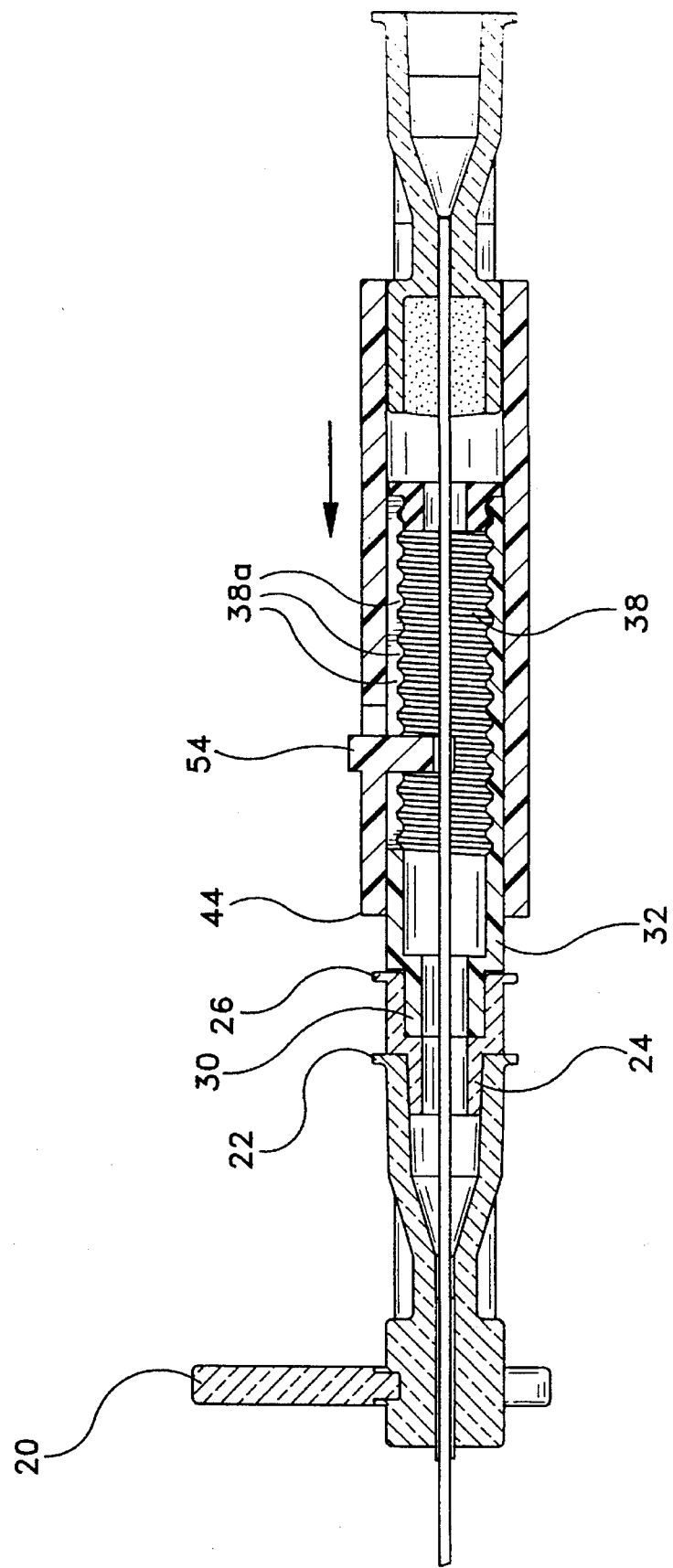
FIG. 5 is a side view of the regulating device, as taken along line 5—5 of FIG. 2, showing the outermost tube in a retracted state relative to the innermost tube.

Referring to FIG. 3, a cap 40 may be provided at the proximal end 29 of the inner robe 32 to be securely mated to the proximal end via an appropriately sized male fitting portion 42. It will be appreciated that the cap 40 may be inserted into the distal end 29 of the inner tube 32 during assembly, such that the inner tube 32 will be disposed within the interior of the outer tube 51, with the cap 40 positioned proximally of the mating portion 70 of the actuating tab 50. In this manner, the inner tube 32 is prevented from inadvertent withdrawal from the outer tube 51 by a blocking action created between the mating surface 70 and the cap 40 (see FIG. 4). As the spinal needle 12 is fitted to the proximal end 46 of the outside tube 51, the spinal needle 12 is disposed through the center of cap 40 via an opening 41.

Operation of the regulating device 10 will now be explained with reference to FIGS. 1–12. As previously explained, the regulating device 10 can be provided either as part of the CSE set including the epidural needle 14 and spinal needle 12, or the device may be provided for use with an individual spinal needle or epidural needle separately sourced, or with a prematched CSE set separately sourced. For instance, the device 10 can be preattached or otherwise form an integral component of either a separately sourced epidural needle 14 or separately sourced spinal needle 12. For instance, the device 10 can form the hub portion of a spinal needle 12.

If, for example, the device is provided with a separately sourced CSE set, the epidural needle 14 is first affixed to the inner tube 32 via the hub fitting 25 as previously described, with the inner tube 32 thereafter slid through the outer tube 51. The neck portion 54a and mating portion 70 of the actuating tab 50 will slide through the axial opening 36 disposed in the inner tube 32, with the cap 40 thereafter fitted to the distal end 29 of the inner tube to secure the inner tube against inadvertent withdrawal of the outer tube 51. The spinal needle 12 may thereafter be fitted to the outer tube 51 and inserted through the hole 41 in the cap 40. The spinal needle will project through the interiors of both the outer tube 51 and inner tube 32, so that the spinal needle 12 is disposed through the lumen 15 of the epidural needle 14. It will be understood that if provided as part of a CSE set, the regulating device 10 may be pre-assembled together with the spinal needle 12 and epidural needle 14.

Figure 11:
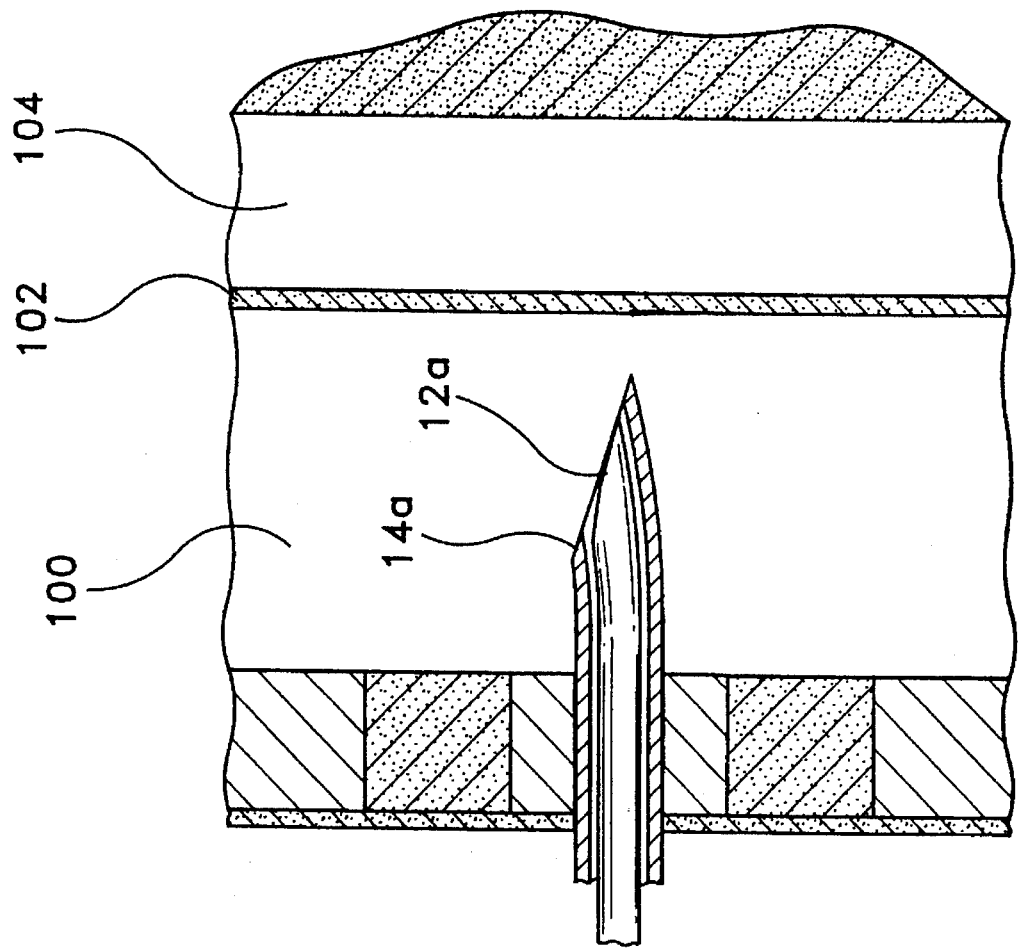
FIG. 11 is a side view illustrating placement of a spinal needle within the lumen of the epidural needle and alignment of the distal tips of both needles prior to extension of the spinal needle.

In order to provide the practitioner with an effective way to gauge the axial extension of the spinal needle 12 relative to the epidural needle 14, the dimensions of the various components such as the inner tube 32 and outer tube 51 may be chosen so that in a first locked position of the actuation tab 50, the distal tip 12a of the spinal needle is aligned with the distal tip 14a of the epidural needle, as illustrated in FIG. 11. As a practical matter, this may be accomplished by designating one of the groove elements 38a which is engaged by the mating portion 70 as corresponding to alignment between the distal tips 12a, 14a of the spinal and epidural needles 12, 14. Additionally, the distal end 44 of the outer tube 51 may be aligned with the individual markings 34a to assist the practitioner with determining relative extension of the spinal needle 12. By correlating one of the individual markings 34a on the inner tube to the designated groove element 38a to indicate when the distal points are aligned, the practitioner is provided with the ability to visually regulate the extension of the spinal needle 12.

In use, with the spinal and epidural needles aligned as previously described, the set is inserted into the epidural space 100 of the patient until the distal point 14a of the epidural needle is positioned by the practitioner in an appropriate location in the epidural space. Note that in this position, outer tube 51 is extended relative to the inner tube 32 so that the the spinal needle 12 is in a retracted state (FIGS. 1 and 4), with the distal tips 12a, 14a of the spinal and epidural needles being aligned, and the mating portion 70 of the actuation tab locked with an individual groove element 38a to maintain the position of the needles.

When the epidural needle has been properly positioned, the finger tab 54 may be activated (depressed) by the practitioner, releasing the mating portion 70 from engagement with the structured surface 38, thereby permitting the outer tube 51 to be axially slidable in the distal direction with respect to the inner tube 32, all with a one-handed effort by the practitioner. The inner tube 32, itself fixed to the epidural needle 14, will remain fixed relative to the patient. As earlier described, a practitioner may additionally utilize wing collar 20 to provide additional support to the epidural needle 14, if need or desire dictate.

Figure 12:
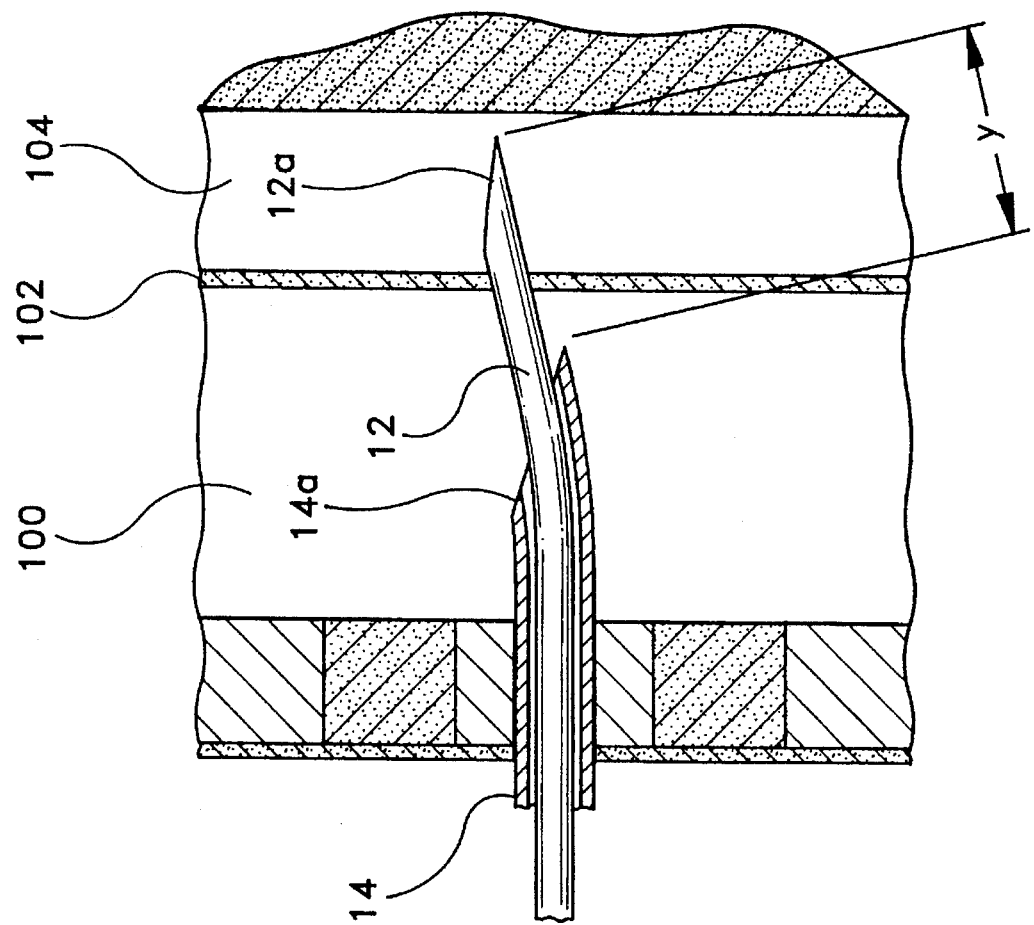
FIG. 12 is a side view illustrating extension of the spinal needle through the dura mater of a patient into the subarachnoid space.

By continuing to slide the tube 51 distally axially forward, the spinal needle 12 will be extended through the epidural needle 14 (FIGS. 2 and 5) so as to puncture the dura mater 102 and come to rest in the subarachnoid space 104 (FIG. 12). Again, the practitioner may monitor the relative position of the distal end 44 of the outer tube 51 relative to the markings 34 as a means to assess relative insertion of the spinal needle. As earlier described, the dimensions of the various components may be chosen and selected as need or desire dictate so that the spinal needle 12 will have a relative extension "X" (see FIG. 2) relative to the spinal needle 14 when the outer tube 51 has been slid axially forward to a maximum position. Intermediate extension positions "Y" (see FIG. 12) may be selected by the practitioner based on the relative position of the distal end 44 of the outer tube 51 to the inner tube 32.

Upon selecting the appropriate position, the practitioner will deactivate (release pressure against) the finger tab 54, causing the actuating tab 50 to be biased upwards, forcing the mating portion 70 to engage one of the various groove elements 38a to lock the position of the outer tube 51 relative to the inner tube 32. If a stylet has been provided, the same may be removed by the practitioner to detect for CSF. It will also be appreciated that by providing a rotating fit between the male luer fitting 24 and hub 22 of the epidural needle 14, and/or a rotating fit between the male luer extension 30 of the inner tube and the hub fitting 25, the practitioner will be able to rotate the spinal needle in all four quadrants of the subarachnoid space 102 while maintaining the spinal needle in locked position relative to the epidural needle. Thus, a one-handed operation is easily achieved.

Thus, it will be seen that the regulating device 10 provides the practitioner with a ready and sure way to practice a CSE procedure in a safe and sure manner. The device is easily operable with a one-handed effort and will guide the practitioner to accurate spinal needle extensions while providing him or her with smooth, steady sliding action and, hence, valuable tactile feedback. The spinal needle may be easily manipulated in the locked position improving safety and alleviating problems previously encountered in the procedure.

It will be appreciated and understood by those skilled in the art that additional and further forms of the invention may be devised without departing from the spirit and scope of the appended claims, the invention not being limited to the specific embodiments shown.

What is claimed is:

1. A device for regulating the extension of a spinal needle relative to an epidural needle, comprising:

a first member for securing said epidural needle;

a second member slidably disposed relative to said first member for securing said spinal needle; and an actuating tab forming a selectably fixed connection between said first and second members, said actuating tab having a locked position wherein said first member is locked relative to said second member and an unlocked position wherein said second member is slidable relative to said first member.

2. The device of claim 1 wherein said second member defines an internal cavity, said first member slidingly disposed within said internal cavity.

3. The device of claim 1, wherein said first member is a tube.

4. The device of claim 1, wherein said second member is a tube.

5. The device of claim 2, wherein said internal cavity comprises a plurality of planar surfaces substantially circumferentially disposed about the central axis of said second member, said first member comprising an exterior surface in point contact with said planar surfaces.

6. The device of claim 2, further comprising a retention cap fixed adjacent to an end of said first member for preventing withdrawal of said first member from the cavity of said second member.

7. The device of claim 1 wherein said device is integral with a hub of said spinal needle.

8. A device for regulating the extension of a spinal needle relative to an epidural needle, comprising:

an inner tube having proximal and distal ends and defining an exterior surface and an interior surface, said epidural needle securable to said distal end;

an outer tube having proximal and distal ends and defining a cavity, the exterior surface of said inner tube substantially slidably disposed within the cavity of said outer tube, the hub of said spinal needle securable to the proximal end of said outer tube; and an actuating tab mounted on said outer tube and forming a selectably fixed connection between said inner tube and said outer tube, said actuating tab movable between a locked position wherein said inner tube is axially fixed relative to said outer tube and an unlocked position wherein said outer tube is axially slidable relative to said inner tube to vary the axial extension of said spinal needle relative to said epidural needle.

9. The device of claim 8, wherein the interior surface of the inner tube comprises a plurality of locking formations disposed along the axis of the inner tube.

10. The device of claim 9, wherein said plurality of locking formations comprise grooves formed on at least a portion of the interior surface of the inner tube.

11. The device of claim 8, wherein said actuating tab comprises:

an arm member having a first end resiliently mounted to said outer tube and an inner tube engaging portion mounted to a second end of said arm member, said inner tube engaging portion disposed through the exterior surface of said inner tube in selective engagement with the interior portion of said inner tube.

12. The device of claim 11, wherein the said inner tube engaging portion comprises a mating surface disposed for user-selectable contact with the interior surface of said inner tube.

13. The device of claim 12, wherein said mating surface comprises a groove dimensioned to mesh with the locking formations formed along the axis of the inner tube.

14. The device of claim 8, wherein said outer tube includes a plurality of markings formed along the axis of the outer tube for gauging the axial position of said inner tube relative to said outer tube.

15. The device of claim 8, wherein said epidural needle is secured to said inner tube by a fitting located at the distal end of the inner tube.

16. The device of claim 8, wherein the cavity of said outer tube comprises a plurality of planar surfaces substantially circumferentially disposed around the central axis of the outer tube, wherein the exterior surface of said inner tube is configured for point contact with said planar surfaces.

17. A device for regulating the extension of a spinal needle relative to an epidural needle, comprising:

an inner tube for securing the epidural needle, said inner tube comprising an exterior surface and an interior surface, said inner tube defining an opening disposed along the axis of the inner tube, the interior surface defining a plurality of locking formations formed along the axis of the inner tube;

an outer tube for securing the spinal needle, said outer tube comprising an internal cavity defined by a plurality of surfaces substantially circumferentially disposed around the central axis of the outer tube, the exterior surface of said inner tube disposed for sliding point contact with said plurality of surfaces; and an actuating tab mounted to said outer tube and forming a selectably fixed connection between said inner tube and said outer tube, said actuating tab comprising an arm portion having a first end biasingly mounted to said outer tube and a second end comprising a mating portion disposed through the axial opening of said inner tube;

wherein said arm portion is biasingly movable between a first position wherein said mating portion is engaged with said locking formations to secure said inner tube in axial relation with said outer tube and a second position wherein said mating portion is disengaged from said locking formations so that said outer tube is axially slidable relative to said inner tube.

18. A device for regulating the extension of a spinal needle relative to an epidural needle, comprising:

a pair of substantially concentrically disposed sliding members, each of said epidural needle and said spinal needle separately affixable to one of said sliding members; and an actuating tab forming a selectably fixed connection between said sliding members, said actuating tab having a locked position wherein said sliding members are locked relative to one another and an unlocked position wherein said sliding members are slidable relative to one another.

19. The device of claim 18 wherein said device is integral with a hub of said spinal needle.

20. A method for regulating the extension of a spinal needle relative to an epidural needle, comprising the steps of:

forming a user-regulatable combined spinal epidural needle set by separately affixing each of said spinal needle and said epidural needle to a pair of substantially concentrically disposed sliding members, wherein said spinal needle is slidingly disposed in the lumen of said epidural needle;

deflecting an actuating tab forming a selectably fixed connection between said pair of substantially concentrically disposed sliding members; and moving the sliding members relative to one another to regulate the extension of said spinal needle relative to said epidural needle.

21. The method of claim 20, wherein the step of separately affixing each of said spinal needle and said epidural needle to said pair of concentrically disposed sliding members includes the steps of affixing said epidural needle to an innermost sliding member and affixing said spinal needle to an outermost sliding member.

22. The method of claim 21, wherein said regulating the extension of said spinal needle relative to said epidural needle further comprises the step of moving said outermost sliding member relative to a set of markings formed on said innermost sliding member, said markings calibrated to the degree of extension of said spinal needle relative to said epidural needle.

23. The method of claim 20, further comprising the step of placing said combined spinal epidural needle set in the epidural space of a patient subsequent to said step of separately affixing.

24. The method of claim 20, further including the step of forming sliding surfaces on each of said sliding members, the sliding surfaces disposed in point contact with one another.

25. The method of claim 20, further comprising the step of forming a plurality of locking formation on a portion of one of said sliding members, said actuating tab being disposed for engagement with one of said plurality of locking formations.

* * * * *